(12) United States Patent
Esteve et al.

(10) Patent No.: US 8,900,872 B2
(45) Date of Patent: Dec. 2, 2014

(54) DIAGNOSTIC TEST CALIBRATION ADJUSTMENT METHOD

(75) Inventors: Frederic Esteve, Paris (FR); Lydie Nicoud, La Celle Saint-Cloud (FR)

(73) Assignee: Diagnostica Stago, Asnieres (FR)

( * ) Notice: Subject to any disclaimer, the term of this patent is extended or adjusted under 35 U.S.C. 154(b) by 0 days.

(21) Appl. No.: 12/680,998

(22) PCT Filed: Oct. 2, 2008

(86) PCT No.: PCT/FR2008/001379
§ 371 (c)(1),
(2), (4) Date: Apr. 29, 2010

(87) PCT Pub. No.: WO2009/077678
PCT Pub. Date: Jun. 25, 2009

(65) Prior Publication Data
US 2010/0227347 A1     Sep. 9, 2010

(30) Foreign Application Priority Data

Oct. 4, 2007    (FR) ...................................... 07 06975

(51) Int. Cl.
*G01N 33/00*    (2006.01)

(52) U.S. Cl.
USPC ............................................ 436/10; 436/69

(58) Field of Classification Search
USPC .................................................... 436/10, 69
See application file for complete search history.

(56) References Cited

U.S. PATENT DOCUMENTS

| | | |
|---|---|---|
| 5,138,034 A | 8/1992 | Uemura et al. |
| 7,797,980 B2 | 9/2010 | Ciotti et al. |
| 2005/0136449 A1 | 6/2005 | Hanson et al. |
| 2007/0020765 A1 | 1/2007 | Zander et al. |
| 2009/0239306 A1 | 9/2009 | Okuda et al. |

FOREIGN PATENT DOCUMENTS

| | | |
|---|---|---|
| EP | 0408029 A1 | 1/1991 |
| EP | 1092157 B1 | 4/2001 |
| EP | 1544621 A1 | 6/2005 |
| JP | 64-91061 A | 4/1989 |
| JP | 3-128398 A | 5/1991 |
| JP | 2003-294761 A | 10/2003 |
| JP | 2004528534 A | 9/2004 |
| JP | 2006234675 A | 9/2006 |
| JP | 2009-501324 A | 1/2009 |
| WO | 95/12127 | 5/1995 |
| WO | 02/052276 | 7/2002 |
| WO | 02052276 A2 | 7/2002 |

OTHER PUBLICATIONS

Giesen "A calibrated automated tool to assess the thrombotic-haemostatic system", CLI, 2005.*
Edlund et al. "A proposed stoichiometrical calibration procedure to achieve transferability of D-dimer measurements and to characterize the performance of different methods", Clinical Biochemistry, 39 (2006) 137-142.*
William F. Brien et al., "In-house Calibration of the International Sensitivity Index or Calibration Curve for Determination of the International Normalized Ration", Archives of Pathology & Laboratory Medicine, Chicago, IL, US, vol. 128, No. 3, Mar. 1, 2004, XP002389073, pp. 308-312.
International Search Report dated Jul. 8, 2009, from corresponding PCT application.
Siemens, "Turbiquant Fibrinogen and Turbiquant Antithrombin III", OWIZ G35 C0501 (821).
Stago Liatest D-Di, "D. Dimer & Fibrinogen Degradation Products".

* cited by examiner

*Primary Examiner* — Monique Cole
(74) *Attorney, Agent, or Firm* — Young & Thompson

(57) ABSTRACT

A method is provided for adjusting either the signal measured or activity calculated by an instrument or a predefined calibration curve for a medical diagnostic test, performed on an instrument with pre-calibrated reagents. A calibration adjuster for a blood clotting diagnostic test is further provided.

11 Claims, No Drawings

DIAGNOSTIC TEST CALIBRATION ADJUSTMENT METHOD

BACKGROUND OF THE INVENTION

1. Field of the Invention

The present invention relates to a direct or indirect method for adjusting the predefined calibration on reagents suitable for performing diagnostic tests in the field of medical biology and more specifically that of haemostasis.

2. Description of the Related Art

Haemostasis is considered to be a set of physiological mechanisms involved in preventing and stopping bleeding.

Haemostasis is frequently compared to scales, as blood fluidity is maintained by means of a balance between clotting factor activators and inhibitors.

Any disruption in this balance will tip the scales towards a pathological process: thrombosis, resulting from the formation of a clot liable to be caused by inhibitor deficiency, or haemorrhaging resulting from bleeding liable to be caused by clotting factor deficiency.

Analysing and assaying clotting activating or inhibiting factors thus makes it possible to diagnose predisposition or risks of thrombosis or haemorrhaging in various clinical situations.

These tests are mainly performed routinely in testing laboratories or hospitals, in a semi-automated or automated manner.

Generally, depending on the tests performed and instruments used, the results consist either of a signal measured by the instrument or of a biological activity calculated by the instrument.

As for most biological tests performed on test systems, when performing an automated haemostasis test, a calibration is required to calculate the level or activity of the factor under study directly. These calibration data are generally obtained using calibrators with a well characterised activity or concentration of the target test substance and on the basis of which calibration curves can be defined to assign a concentration or activity to a given signal intensity.

However, insofar as the same test may frequently be performed on systems from different ranges, it is frequent to observe between-instrument variability. This variability does not always enable direct comparison, for the same test, of the results obtained on different apparatuses always using the same standard calibration.

Moreover, since a large number of reagents are in liquid form, they may be more susceptible to the ageing phenomenon than reagents in freeze-dried form. For this reason, even though these reagents remain functional for a certain time, the sensitivity thereof may nevertheless decrease partially or vary over time.

This results in a difficulty interpreting the results obtained using the same reagent but arising from tests performed over different periods.

The application US 2007/0020765 describes a method for standardising the clotting time of a sample, wherein at least two calibrators are used, for which standard clotting times have been predetermined in the same test system as that applied to the sample, and on the basis whereof a calibration curve is defined between the predetermined standard times and the actual times measured for the same calibrators, in the test used.

The clotting time measured in the sample is converted into a standardised clotting time using the calibration curve defined.

Therefore, this method consists of creating a calibration locally whenever a new kit is used to measure a clotting time in a haemostasis test.

SUMMARY OF THE INVENTION

The aim of the present invention is to provide a method for adjusting test instruments and associated pre-calibrated reagents, said method making it possible to limit or avoid fluctuations of the results obtained over time and/or according to the type of instrument used for the tests.

The present invention thus relates to a method for adjusting either the signal measured or activity calculated by the instrument or a predefined calibration curve (pre-calibration curve) for a medical biology diagnostic test, performed on an instrument with pre-calibrated reagents, comprising the following steps:

(i) defining a signal or activity value, referred to as the standard value, for a single or for two calibration adjuster(s) having a predetermined concentration or activity of a compound under test, and measuring for said adjuster(s) the difference between the standard signal or activity value(s) and the value(s) either of the signal measured by the instrument or the activity value(s) calculated using the pre-calibration curve and, if the difference measured has an acceptable value, (ii) adjusting the signal measured by the instrument or the value of the activity calculated by the instrument or adjusting the value(s) of the pre-calibration curve such that the value of the signal measured or activity calculated on the pre-calibration curve for the single or both adjuster(s) is brought back to a signal or activity value identical to the standard signal or activity value determined in step (i) for the single adjuster or for each of the two adjusters, (iii) applying the same adjustment as that described in (ii) to all the samples tested the signal or activity of which is measured with said pre-calibrated reagents.

Preferentially, the method according to the invention is used in a blood clotting investigation test.

DETAILED DESCRIPTION OF THE INVENTION

The term measured difference having an "acceptable value" refers to a difference remaining between two values of the range of values considered to be admissible by a person skilled in the art, for the reagent and instrument used.

This difference may vary according to the sensitivity of the test used and the order of magnitude of the signals measured.

For this reason, the limit above which the adjustment of the pre-calibration would no longer be acceptable must be defined in relation to the type of test and instrument used.

A person skilled in the art accustomed to analysing the results given by test automatic apparatuses can readily detect, when performing tests, the values from which the results are considered to be abnormal, whether due to the reagent used or the instrument.

A person skilled in the art is thus capable of defining differences between the standard signal or activity values and the signal values measured by the instrument or activity values calculated on the pre-calibration curve according to step (i) of the method according to the invention, which are sufficiently small so as not to conceal anomalies of the reagents or apparatuses used.

Preferably, the difference measured is not more than 20 to 30%.

According to one preferred alternative embodiment, the method according to the invention is performed with a single adjuster.

According to one particular embodiment of the invention, the adjustment, by means of a single adjuster, of a signal measured as part of a predetermined test, according to steps (i) and (ii) of the method according to the invention can be performed as follows:

for step (i) defining the standard value, the following procedure is applied:

The standard signal value assigned to the adjuster is calculated on the basis of the results determined during the step for determining the pre-calibration of the product in question. The determination of the pre-calibration consists of running standards with known levels of the test substance under assay (test compound) on a panel of a plurality of instruments. Each of the standards is run in duplicate, in triplicate or in quadruplicate on each instrument.

At the same time, the adjuster to be titrated for the signal is also run simultaneously in duplicate, in triplicate or in quadruplicate on the same instruments.

The arithmetic mean, the truncated mean or the median are then calculated outside the instrument on all the signal values obtained, separately for each standard and for the adjuster.

The determination of the pre-calibration equation is calculated outside the instrument by means of least squares regression on the various pairs (mean or median signal; standard concentration).

The standard signal value of the adjuster corresponds respectively to the arithmetic mean, the truncated mean or the median of all the signal values measured on this adjuster as part of the pre-calibration determination according to the calculation method selected. The standard signal value calculated for this adjuster is only valid for the specific batch of pre-calibrated product.

Therefore, the standard signal or activity value (see hereinafter) of the adjuster or adjusters can thus be performed prior to and independently from the diagnostic test. The standard signal (or activity) value of the adjuster (or adjusters) can therefore be given to the user of the diagnostic test with the batch of reagents to be used and the adjuster (adjusters).

for steps (ii) and (iii) for adjusting the values measured for the adjuster and the test samples, the following procedure is followed:

The standard signal value assigned to the adjuster for its batch of pre-calibrated product is referenced S. When this adjuster is run in duplicate, in triplicate or in quadruplicate on an instrument with this batch of pre-calibrated product, the instrument calculates the signal T which corresponds, according to the calculation method selected to determine S, to the arithmetic mean, to the truncated mean or to the median of these various measured signals. If the difference between S and T meets the acceptance criteria known by the instrument, the instrument calculates an adjustment coefficient C which is equal to the ratio of S over T (C=S/T). By multiplying the signal T measured by the instrument for the adjuster by this adjustment coefficient C equal to S/T, the adjusted value of the adjuster signal is equal to S. Similarly, when the samples under assay are run on the same instrument, the signal measurements obtained are adjusted by multiplying these measurements by the adjustment coefficient C. The concentration or activity of the test substance under assay is then calculated by applying the pre-calibration to this adjusted signal value.

According to a further particular embodiment of the invention, the adjustment by means of a single adjuster is performed on the activity calculated by the test instrument, according to steps (i) and (ii) of the method according to the invention, as follows:

for step (i) for defining the standard value

The standard activity value is assigned to the adjuster by a titration. For this purpose, a plurality of tests is performed with one or various batches of pre-calibrated reagents on various systems. The number of determinations may vary according to the parameter in question but is always greater than or equal to 3. This titration is separate from the pre-calibration determination.

The adjuster (which is, for example, a control/calibrator type freeze-dried plasma-based reagent with excipient)) is tested in duplicate, in triplicate or in quadruplicate during each determination, the standard activity thereof is deduced by reading the signals measured on the pre-calibration.

The arithmetic mean, the truncated mean or the median is then calculated outside the instruments on all the activities obtained with each batch of pre-calibrated reagent on each automatic apparatus for each adjuster. The standard activity value or titre of the adjuster corresponds, according to the calculation method adopted, to the arithmetic mean, the truncated mean or the median of all the activity values measured on the adjuster as part of this titration. The standard activity value calculated for this adjuster may be valid for one or a plurality of batches of pre-calibrated product.

Whenever possible, the titration of the adjuster is correlated with the international standard of the parameter. This ensures, in addition to the homogeneity in the system in question, consistency with the international system.

for steps (ii) and (iii) for adjusting the activity measured:

The titre assigned to the adjuster is referenced S. When this adjuster is run in duplicate, in triplicate or in quadruplicate on an instrument with the batch or batches of pre-calibrated products corresponding thereto, the instrument calculates, on the basis of the signal measured, the activity T which corresponds, according to the calculation method selected to determine S, to the arithmetic mean, to the truncated mean or to the median of these various measured signals. If the difference between S and T meets the acceptance criteria known by the instrument, the instrument calculates an adjustment coefficient C which is equal to the ratio of S over T (C=S/T). In this way, by multiplying the signal T measured by the instrument for the adjuster by this adjustment coefficient C equal to S/T, the adjusted value of the adjuster signal is equal to S. Similarly, when the samples under assay are run on the same instrument, the signals measured are converted to activities by means of the reagent pre-calibration equation. The activities obtained are then adjusted by multiplying same by said adjustment coefficient C.

An adjuster used within the scope of the method according to the invention is a composition for:

during the use of a new reagent batch, adjusting the test results returned, to the instrument used for performing the test while using the pre-calibration. The purpose is to realign the controls when they are systematically offset.

over time, compensating for a loss of sensitivity of the reagent for example due to the ageing thereof. As mentioned above, this point is particularly applicable to liquid reagents which are less stable over time than freeze-dried reagents.

The composition of the adjuster with respect to clotting factors or other constituents is defined according to the test performed.

The adjuster must contain at least the compound studied in the test used, the concentration or activity whereof is predetermined.

In the case of a blood clotting investigation test, the adjuster preferably consists of stabilised freeze-dried plasma or a stabilised freeze-dried plasma pool.

It may also consist of purified or semi-purified plasma proteins, said proteins providing the supply of factors required to perform the reaction produced as part of the test performed and further comprising the compound under study (also referred to as the factor under study), the concentration or activity whereof is predetermined.

The concentration (or activity level) of the factor under study, used in the adjuster must be selected so as to minimise the influence of potential background noise on the correction of the pre-calibration.

For this purpose, the test compound concentration or activity of the adjuster is defined such that the signal/background noise ratio is high.

According to the type of test used, the relationship between the signal measured and the activity or concentration of the compound under study of the adjuster is different. For this reason, curves with different profiles according to the tests are obtained.

For example, in the case of an antithrombin (AT) assay such as that proposed by the STA-Stachrom ATIII kit, marketed by Diagnostica Stago, the DOD (delta OD) decreases when the ATIII concentration increases.

However, since the ATIII concentration is lower in a pathological situation than in a normal situation, the AT concentration of the adjuster for the implementation of the adjustment method according to the invention will be selected such that the adjuster is positioned in a range covering a pathological value (i.e. low quantity of ATIII).

Conversely, in the case of a protein C assay such as that proposed by the STA-Stachrom Protein C kit (Diagnostica Stago), the adjuster will be positioned in a range corresponding to the normal Protein C concentration, since the signal measured increases proportionally with the quantity of protein C and the normal range is delimited by the upper protein C level values.

In the case of the D-Dimer assay such as for example that performed by the STA-Liatest D-Di kit (Diagnostica Stago), it is observed that the signal increases with the quantity of D-Di. However, in normal situations, the D-Dimer level is lower than in pathological situations. The adjuster according to the invention will thus be selected such that the signal observed is positioned in the pathological range. In the case of the assay using the STA-Liatest kit, the adjustment may have the composition of an STA Liatest Control P or STA Liatest Control N reagent.

The method according to the invention may be used for any type of blood clotting investigation test such as APTT (Activated Partial Thromboplastin Time), PT (Prothrombin time or Quick time) or TT (Thrombin time) or any other conventional enzymological test based on optical density (OD) or time measurements.

It may also be applied to dispersed solid phase immunological assay tests, based on the photometric measurement of the increase in turbidity of a microsphere suspension.

The examples hereinafter illustrate the present invention.

Example No. 1

Study of the Adjustment of the Pre-Calibration of STA Liatest D-Di: Feasibility of One-Point DOD Correction on Loss of Reactivity Associated with Reagent Ageing The method according to the invention is applied to a test marketed under the name STA-Liatest D-Di by Diagnostica Stago.

It consists of an immunoturbidimetry plasma D-Dimer (D-Di) assay kit using latex microspheres coated with two anti-D-Dimer monoclonal antibodies.

In the presence of the test substance (D-Dimer), the antigen/antibody type reaction induces agglutination of the latex particles, which induces an increase in the turbidity of the reaction mixture.

This is measured on an STA range analyser (Diagnostic Stago) in kinetic mode at 540 nm for 140 seconds, according to the instructions in the kit package insert.

The increase in absorbance is proportional to the D-Dimer concentration of the sample under test.

The kit reagents are liquid, ready-to-use.

For each reagent batch, pre-calibration by provided by a barcoded label. The pre-calibration coefficients of the batch used are thus sent directly to the instrument by simply scanning the barcoded label.

Control plasmas (Positive control and Negative control) are used to validate the calibration and the assay runs.

The D-Di concentration measurement was performed a first time at T=0 (Table 1) on 4 plasma samples with a specific batch of STA Liatest D-Di, and a second time on the same samples and with the same batch, 20 months later (at T=20 months) (Table 2).

The plasmas used are standard plasmas with defined target values for the parameter measured (D-Di): (target value=mean value determined on a large number of experimental tests)

RIN2 is a plasma with a target D-Di value of 0.58 µg/ml

PN2 is a plasma with a target D-Di value of 0.83 µg/ml.

LCP is a pathological control plasma (STA Liatest Control P), targeted at 2.40 µg/ml D-Di.

P2 is a further pathological plasma.

The adjustment point used in this example is the "STA Liatest Control P" (LCP).

The DODs are measured on 10 STA range instruments.

The DODs measured by each instrument were corrected by a coefficient which is calculated by the ratio of the standard DOD of this reagent, equal to 0.129, over the mean DOD of a quadruplet (×4) obtained on each instrument.

This standard DOD of 0.129 corresponds to the mean DOD obtained on a batch of STA Liatest Control P (LCP in this example), during the determination of the pre-calibration of the batch of STA Liatest D-Di used.

Four concentration levels were tested on a specific STA Liatest D-Di batch pre-calibrated at T=0.

Tables 1 and 2 give the results obtained at T=0 (table 1) and at T=20 months (table 2) respectively.

The results in table 3, which are those obtained at T=20 months after adjustment by the LCP, are very similar to those obtained initially at T=0 (table 1).

In conclusion: the one-point adjustment of the DODs makes it possible to retrieve, 20 months later with the reagent pre-calibrated at T=0 (Table 3), mean concentrations equivalent to those obtained at T=0 (Table 1).

Therefore, the one-point adjustment of the DODs measured is effective for compensating for the loss of sensitivity of STA Liatest D-Di.

TABLE 1

D-Dimer concentrations (µg/ml) obtained at
T = 0 with pre-calibrated reagent

|  | RIN2 | PN2 | P2 | LCP |
|---|---|---|---|---|
| MIN | 0.55 | 0.79 | 2.30 | 2.33 |
| MAX | 0.66 | 0.88 | 2.56 | 2.53 |
| MEAN | 0.59 | 0.84 | 2.46 | 2.45 |
| SD | 0.032 | 0.032 | 0.079 | 0.067 |
| CV (%) | 5.47 | 3.86 | 3.20 | 2.73 |

TABLE 2

D-Dimer concentrations (µg/ml) obtained at T =
20 months with pre-calibrated reagent

|  | RIN2 | PN2 | P2 | LCP |
|---|---|---|---|---|
| MIN | 0.50 | 0.71 | 1.98 | 2.00 |
| MAX | 0.60 | 0.79 | 2.19 | 2.17 |
| MEAN | 0.54 | 0.75 | 2.11 | 2.10 |
| SD | 0.029 | 0.028 | 0.064 | 0.054 |
| CV (%) | 5.43 | 3.77 | 3.04 | 2.59 |

TABLE 3

D-Dimer concentrations (µg/ml) obtained at T =
20 months with pre-calibrated reagent and after DOD
adjustment on each instrument with LCP

|  | RIN2 | PN2 | P2 | LCP |
|---|---|---|---|---|
| MIN | 0.57 | 0.82 | 2.40 | REF |
| MAX | 0.66 | 0.90 | 2.61 |  |
| MEAN | 0.60 | 0.85 | 2.49 |  |
| SD | 0.028 | 0.028 | 0.070 |  |
| CV (%) | 4.67 | 3.29 | 2.82 |  |

TABLE 4

Free Protein S concentrations (%) obtained with the calibration
of each instrument with an internal calibrator

| Results | LCP | 53% Plasma | LCN | Stago Pool | Unit plasma |
|---|---|---|---|---|---|
| MIN | 25.07 | 50.07 | 78.20 | 88.24 | 86.71 |
| MAX | 27.09 | 55.82 | 84.85 | 97.89 | 113.21 |
| MEAN | 25.75 | 53.00 | 80.88 | 93.96 | 103.54 |
| SD | 0.63 | 1.80 | 2.32 | 2.81 | 7.63 |
| CV | 2.45 | 3.40 | 2.87 | 2.99 | 7.36 |

TABLE 5

Free Protein S concentrations (%) obtained with commercial
pre-calibration applied without any adjustment

| Results | LCP | 53% Plasma | LCN | Stago Pool | Unit plasma |
|---|---|---|---|---|---|
| MIN | 24.35 | 46.77 | 70.57 | 81.89 | 77.84 |
| MAX | 27.51 | 57.79 | 94.48 | 104.71 | 125.35 |
| MEAN | 26.05 | 52.72 | 80.58 | 93.79 | 103.82 |
| SD | 0.92 | 3.49 | 7.39 | 7.29 | 12.18 |
| CV | 3.55 | 6.62 | 9.16 | 7.77 | 11.74 |

TABLE 6

Free Protein S concentrations obtained with commercial pre-
calibration after one-point DOD adjustment on the Stago pool

| Results | LCP | 53% Plasma | LCN | Stago Pool | Unit plasma |
|---|---|---|---|---|---|
| MIN | 24.11 | 51.03 | 77.05 | REF | 88.86 |
| MAX | 26.78 | 54.08 | 84.78 |  | 113.03 |
| MEAN | 26.07 | 52.68 | 80.24 |  | 103.47 |
| SD | 0.58 | 1.04 | 2.45 |  | 6.87 |
| CV | 2.22 | 1.97 | 3.06 |  | 6.64 |

Example No. 2

Pre-Calibration Adjustment Study for STA Liatest Free PS

The study is performed using another kit marketed by Diagnostic Stago, STA Liatest Free PS.

The kit is of the same type as the previous kit, for the quantitative assay of free protein S using an immunoturbidimetric method.

The measurement is made on 10 STA instruments.

It is performed on different plasma batches, i.e.:

A normal control plasma and a pathological control plasma (LCN and LCP: STA Liatest Control N+P−).

A 53% plasma: this is a freeze-dried pathological plasma.

A frozen unit plasma pool (Stago pool).

A frozen unit plasma.

Table 4 gives the free protein S concentrations (%) obtained with the calibration of each apparatus with an internal calibrator.

Table 5 gives the free protein S concentrations (%) obtained with the commercial pre-calibration applied without adjustment: non-adjusted pre-calibration.

Table 6 gives the free protein S concentrations (%) obtained with the commercial pre-calibration after one-point DOD adjustment on the Stago pool: adjusted pre-calibration.

The between-instrument variability measured on 10 STAs for concentrations above 50% is very marked with the pre-calibrated STA Liatest Free PS (non-adjusted pre-calibration). The between-instrument CV on LCN is 9.16% on the non-adjusted pre-calibration as opposed to 2.87% on the calibration of each instrument and 2.45% on the adjusted pre-calibration.

Similarly, the between-instrument variability is improved on the 53% plasma (in the decisive range) and on the 26% LCP when the pre-calibration is adjusted:

53% plasma: CVinstrument cal.=3.40%. CVnon-adjusted pre-cal.=6.62%, CVadjusted pre-cal.=1.97%.

26% LCP plasma: CVinstrument cal.=2.45%. CVnon-adjusted pre-cal.=2.45%, CVadjusted pre-cal=2.22%.

Consequently, at all concentration levels, one-point pre-calibration adjustment gives between-instrument CV values which are:

superior to those obtained with non-adjusted pre-calibration at least equivalent to those obtained with calibration of each instrument with an internal calibrator.

In conclusion, the between-instrument variability is markedly improved on STA Liatest Free PS with the one-point DOD adjustment method according to the invention.

Example No. 3

STA-Fib 2 pre-calibration adjustment study: feasibility of correction of levels (g/l) on alignment of controls (closest value obtained to target value=centre of range provided for a given system).

The method according to the invention was applied to a test marketed under the name STA-Fib 2 by Diagnostica Stago.

It consists of a plasma fibrinogen assay kit using the Clauss method.

In the presence of excess thrombin, the clotting time of a plasma, diluted in suitable proportions, is inversely proportional to the plasma fibrinogen level.

The kit reagent is freeze-dried. For each reagent batch, pre-calibration by provided by a barcoded label. The pre-calibration coefficients of the batch used are thus sent directly to the instrument by simply scanning the barcoded label.

Control plasmas (normal and hypofibrinogenaemic) are used to validate the calibration and the assay runs.

The plasma fibrinogen level measurement was performed on various control plasmas on a system fleet of 71 machines including around forty STA-R, around ten STAc and around STA-Satellite systems.

The controls used are standard plasmas with the following target values for the parameter measured:
CCN is a plasma with a target value of 2.95 g/l
CCP is a plasma with a target value of 1.30 g/l
HYPER is a plasma with a target value of 5.27 g/l.

The plasma serving as the adjuster was AJP plasma with a target value of 3.20 g/l.

For this study, the levels were measured in n=5 on each instrument tested. On the basis of the values obtained for AJP plasma on each system, the levels were adjusted (using the method described in the present application, for the adjustment on the calculated activity).

The tables below give the mean levels obtained with and without adjustment (levels obtained by pre-calibrating the batch in question) in relation to the target value of the controls under test and the overall standard deviation obtained.

| Without adjustment | CCN target: 2.95 g/l | CCP target: 1.30 g/l | HYPER target: 5.27 g/l |
|---|---|---|---|
| Mean | 2.82 | 1.24 | 5.06 |
| SD | 0.11 | 0.04 | 0.19 |

| With adjustment | CCN target: 2.95 g/l | CCP target: 1.30 g/l | HYPER target: 5.27 g/l |
|---|---|---|---|
| Mean | 2.91 | 1.28 | 5.23 |
| SD | 0.11 | 0.05 | 0.19 |

In conclusion, the adjustment made realigned the levels obtained on the various plasmas in relation to the target value thereof, while retaining a homogeneous standard deviation on the fleet tested.

The invention claimed is:

1. A method for adjusting a signal measured for a blood clotting investigation test that is a dispersed solid phase immunological assay test, performed on an instrument with pre-calibrated reagents, comprising the following steps:
   (i) defining a standard signal value, for one or two calibration adjuster(s) comprising a compound under test having a predetermined concentration or activity;
   (ii) measuring for said adjuster(s) a difference between the standard signal and the value of the signal measured by the instrument;
   (iii) adjusting the value of the signal measured by the instrument such that the value of the signal measured by the instrument is brought back to a signal value identical to the standard signal value determined in step (i) for the single adjuster or for each of the two adjusters; and
   (iv) applying the adjustment of step (iii) to each compound under test.

2. The method according to claim 1, wherein a single adjuster is used.

3. The method according to claim 1, wherein the difference measured according to step (ii) is not more than 20 to 30%.

4. The method according to claim 1, wherein at least one of the adjusters comprises stabilised freeze-dried plasma or a stabilised freeze-dried plasma pool.

5. The method according to claim 1, wherein at least one of the adjusters comprises purified or semi-purified plasma proteins, and further comprises the compound under test, the concentration or activity of the compound under test being predetermined.

6. A method for adjusting a signal measured for a blood clotting investigation test that is a functional investigation test that is a D-Dimer assay test, performed on an instrument with pre-calibrated reagents, comprising the following steps:
   (i) defining a standard signal value, for one or two calibration adjuster(s) comprising a compound under test having a predetermined concentration or activity;
   (ii) measuring for said adjuster(s) a difference between the standard signal and the value of the signal measured by the instrument;
   (iii) adjusting the value of the signal measured by the instrument such that the value of the signal measured by the instrument is brought back to a signal value identical to the standard signal value determined in step (i) for the single adjuster or for each of the two adjusters; and
   (iv) applying the adjustment of step (iii) to each compound under test.

7. The method according to claim 1, wherein the clotting investigation test is an APTT, PT, TT test or an enzymological test.

8. The method according to claim 6, wherein a single adjuster is used.

9. The method according to claim 6, wherein the difference measured according to step (ii) is not more than 20 to 30%.

10. The method according to claim 6, wherein at least one of the adjusters comprises stabilised freeze-dried plasma or a stabilized freeze-dried plasma pool.

11. The method according to claim 6, wherein at least one of the adjusters comprises purified or semi-purified plasma proteins, and further comprises the compound under test, the concentration or activity of the compound under test being predetermined.

* * * * *